US009470658B2

(12) United States Patent
Troy et al.

(10) Patent No.: US 9,470,658 B2
(45) Date of Patent: Oct. 18, 2016

(54) SELF-CONTAINED HOLONOMIC TRACKING METHOD AND APPARATUS FOR NON-DESTRUCTIVE INSPECTION

(71) Applicant: The Boeing Company, Chicago, IL (US)

(72) Inventors: James J. Troy, Issaquah, WA (US); Scott W. Lea, Renton, WA (US); Gary E. Georgeson, Tacoma, WA (US); Karl E. Nelson, Shoreline, WA (US); Daniel James Wright, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 891 days.

(21) Appl. No.: 13/796,584

(22) Filed: Mar. 12, 2013

(65) Prior Publication Data

US 2014/0278221 A1    Sep. 18, 2014

(51) Int. Cl.
| | |
|---|---|
| *G01N 29/04* | (2006.01) |
| *G01C 22/02* | (2006.01) |
| *G01N 29/22* | (2006.01) |
| *G05D 1/02* | (2006.01) |
| *G01N 27/90* | (2006.01) |
| *G01N 29/265* | (2006.01) |

(52) U.S. Cl.
CPC ............... *G01N 29/04* (2013.01); *G01C 22/02* (2013.01); *G01N 27/9013* (2013.01); *G01N 29/225* (2013.01); *G01N 29/265* (2013.01); *G05D 1/0272* (2013.01); *G01N 2291/106* (2013.01)

(58) Field of Classification Search
CPC ...................................................... G01C 22/02
See application file for complete search history.

(56) References Cited

U.S. PATENT DOCUMENTS

| | | | |
|---|---|---|---|
| 6,853,877 B1 | 2/2005 | Slater et al. | |
| 7,848,894 B2 | 12/2010 | Motzer et al. | |
| 8,279,412 B2 | 10/2012 | Motzer et al. | |
| 2007/0096727 A1 | 5/2007 | Rempt et al. | |
| 2013/0024067 A1* | 1/2013 | Troy ....................... | B25J 5/007 701/36 |

OTHER PUBLICATIONS

Yong Liu et al.; "Omni-directional mobile robot controller based on trajectory linearization"; Jun. 20, 2006; Science Direct; pp. 461-479.*
Written Opinion of International Searching Authority, dated Sep. 24, 2015, International Application No. PCT/US2013/076729 (foreign counterpart of the instant patent application).
Liu et al., "Omni-directional mobile robot controller based on trajectory linearization," Robotics and Autonomous Systems, vol. 56, No. 5 (2008), pp. 461-479.
International Search Report and Written Opinion, International Application No. PCT/US2013/076729 (Counterpart to instant application), dated Apr. 8, 2014.

* cited by examiner

*Primary Examiner* — Manuel Rivera Vargas
(74) *Attorney, Agent, or Firm* — Ostrager Chong Flaherty & Broitman P.C.

(57) ABSTRACT

A self-contained, holonomic motion tracking solution for supplementing the acquisition of inspection information on the surface of a structure, thereby enabling the real-time production of two-dimensional images from hand-held and automated scanning by holonomic-motion of non-destructive inspection (NDI) sensor units (e.g., NDI probes). The systems and methods disclosed enable precise tracking of the position and orientation of a holonomic-motion NDI sensor unit (hand-held or automated) and conversion of the acquired tracking data into encoder pulse signals for processing by a NDI scanning system.

22 Claims, 6 Drawing Sheets

SELF-CONTAINED HOLONOMIC TRACKING METHOD AND APPARATUS FOR NON-DESTRUCTIVE INSPECTION

BACKGROUND

This disclosure generally relates to systems and methods for tracking the holonomic motion of an automated tool (such as a non-destructive inspection unit) as it moves over a target area.

Portable non-destructive inspection (NDI) instruments that utilize hand-held sensors are common for conducting manufacturing and in-service inspection of selected areas of composite structures. Most in-service inspection of aircraft structure is done using hand-held sensors. Small parts or areas are occasionally inspected this way during manufacturing as well.

While hand-held sensors are commonly used because they are lower cost, as compared to automated scanning systems, an expert is needed to interpret the resulting signal. In addition, searching for damage or defects by hand while watching for a signal change is time-consuming and is prone to operator error or fatigue. Quantifying the damage takes time as well, since a point-by-point measurement is being made. It is also well known that many hand-held NDI sensor units do not detect smaller damage/flaws that could be detected using scanning that can create images of the area containing the damage. This image-based scanning relies upon correlation of the sensor positional information relative to the sensor data itself. Correlation of single-point NDI data acquired by a hand-held sensor with position is difficult. Also, higher damage detectability limits of common hand-held sensor units mean the inspection cycles are shorter (and costlier) than they could be.

Currently available solutions for tracking of hand-held scanning devices usually track only a single axis in the direction of travel (i.e., one-dimensional motion). This one-dimensional tracking is typically performed using a wheeled rotational encoder. But with free-form movement of the operator's hand providing the motion for the scanning device, there are no guides to ensure that the sensor (e.g., a linear transducer array) is traveling in a straight line. The result is that the one-dimensional tracking of the wheeled encoder may provide very poor tracking of the actual motion of the operator's hand. A skilled operator may be able to partially compensate for this by concentrating on making straight line motions, but humans are not very good at making straight line motions, especially over long distances. Wavy scans are often the result—although this waviness is not apparent to the operator during the scanning process, since the output from the one-dimensional scan will be misleading by appearing to be straight.

Real-time imaging of hand-scan NDI data is currently performed using several different types of position tracking methods, including: single axis rotational encoders, X-Y bridges, scan arms, trackballs, and ultrasonic or optical triangulation are some of the most common. The biggest problems with hand scanning of a single probe are: data positioning (shifts occur depending on the direction of probe movement or where the probe stops) and getting enough passes to cover an area. Drift is also a problem. The two-dimensional images acquired using free-hand motion are usually not very accurate representations of the actual path taken. A linear array, for some methods like ultrasonic and eddy current, will improve the image by making bands of data that accurately represent the relative positions of the data within each band. The biggest problem with hand scanning using linear arrays, however, is maintaining or determining orientation (if not constrained).

During NDI surface scanning applications using hand-held devices, the operator is usually required to maintain a consistent orientation of the scanning device with respect to the direction of travel in order to capture an accurate representation of the scan region. In addition, the operator needs to maintain the velocity below a maximum speed in order to avoid missing data. These requirements can be difficult to accomplish without a measurement system capable of providing feedback to the operator.

These inaccuracies in position measurement, along with the lack of orientation and velocity feedback, have a negative impact on performance. Operators of hand-held scanners may compensate for the inaccuracies in translation and rotation, and the lack of velocity feedback by moving more slowly, which can lead to longer amounts of time needed to acquire useful scan imaging data. This can sometimes lead to re-work to address areas missed during the scan.

There is a need for methods that determine sensor position and orientation in order to obtain correctly aligned NDI images from data acquired during free-form motion.

SUMMARY

The subject matter disclosed hereinafter is directed to methods for real-time, holonomic motion tracking in surface scanning applications using a self-contained device. Holonomic motion is movement that is not subject to motion constraints, and is sometime referred to as free-form motion. As used in this disclosure, a vehicle or device is considered to be holonomic if the controllable degrees of freedom are equal to the total degrees of freedom. Holonomic motion tracking refers to position and orientation measurement on a surface in which the tracked device (e.g., a scanning sensor or sensor array) can translate in any direction and rotate simultaneously. Having a self-contained device that enables tracking of the type of free-form motion produced by human motion of a scanner over a surface enables accurate registration of scan imaging data for the creation of two-dimensional scan images. Since the motion of the tracked device is not constrained by the tracking system, the concept is also applicable to integration with automated devices, such as surface-crawling robots. The systems and methods disclosed in detail below enable precise tracking of the position and orientation of a holonomic-motion NDI sensor unit (hand-held or automated) and conversion of the acquired tracking data into encoder pulse signals for processing by a NDI scanning system.

One aspect of the subject matter disclosed herein is a method for tracking a device that is coupled to a plurality of omni wheels, comprising: (a) converting rotation of each omni wheel into respective encoder data; (b) computing an absolute angle representing an orientation of the device relative to a coordinate system of the surface based in part on the encoder data; (c) computing relative changes in X and Y positions of the device relative to the coordinate system of the surface based in part on the encoder data; and (d) computing an absolute position of the device relative to the coordinate system of the surface based in part on the computed absolute angle and the computed changes in X and Y positions.

A further aspect of the subject matter disclosed herein is a device comprising: a frame; a plurality of omni wheels rotatably coupled to the frame; a plurality of rotational encoders respectively coupled to the plurality of omni wheels; and an inspection unit connected to the frame. In accordance with one embodiment, the plurality of omni wheels are arranged in a four-omni wheel, perpendicular, double-differential configuration. In accordance with a second embodiment, the plurality of omni wheels comprises three omni wheels equidistant from a common center point with axes of rotations at 120 degree angles with respect to each other. In accordance with a third embodiment, the plurality of omni wheels are arranged in a four-omni wheel, bogie configuration.

A further aspect is an inspection system comprising a scanning device, a display device and a computer system, the scanning device and the display device being coupled to communicate with the computer system. The scanning device comprises: a frame; a plurality of omni wheels rotatably coupled to the frame; a plurality of rotational encoders respectively coupled to the plurality of omni wheels for converting rotation of each omni wheel into respective encoder data; and an inspection unit connected to the frame. The computer system is programmed to execute the following operations: (a) computing an absolute angle representing an orientation of the device relative to a coordinate system of the surface based in part on the encoder data; (b) computing relative changes in X and Y positions of the device relative to the coordinate system of the surface based in part on the encoder data; (c) computing an absolute position of the device relative to the coordinate system of the surface based in part on the computed absolute angle and the computed changes in X and Y positions; (d) controlling the inspection unit to acquire inspection data; (e) controlling the display device to display an image in which the inspection data is arranged based on the respective absolute angle and absolute position of the device when each inspection datum was acquired.

Another aspect is a tracking system comprising a movable device and a computer system, the movable device being coupled to communicate with the computer system. The movable device comprises: a frame; a plurality of omni wheels rotatably coupled to the frame; and a plurality of rotational encoders respectively coupled to the plurality of omni wheels for converting rotation of each omni wheel into respective encoder data and some form of motion actuation (such as drive motors and wheels). The computer system is programmed to execute the following operations: (a) computing an absolute angle representing an orientation of the device relative to a coordinate system of the surface based in part on the encoder data; (b) computing relative changes in X and Y positions of the device relative to the coordinate system of the surface based in part on the encoder data; and (c) computing an absolute position of the device relative to the coordinate system of the surface based in part on the computed absolute angle and the computed changes in X and Y positions. In some embodiments the computer may also be used for controlling motion actuation.

Other aspects of self-contained holonomic motion tracking methods and apparatus are disclosed below.

BRIEF DESCRIPTION OF THE DRAWINGS

Reference will hereinafter be made to the drawings in which similar elements in different drawings bear the same reference numerals.

DETAILED DESCRIPTION

The system disclosed in detail below is a multi-dimensional differential odometry-based solution that enables true holonomic surface tracking (i.e., simultaneous multi-dimensional position and orientation tracking) using one of several orientations of omni wheels rotatably mounted to the frame of a hand-held or automated holonomic tracking device. Omni wheels are wheels with small rollers around the circumference, which rollers are rotatable about axes which are perpendicular to the axis about which the main wheel rotates during rolling (also known as the main wheel axle) and tangential to the outer edge of the main wheel. (These rollers are not cylindrical. Instead, they are larger in the middle with a shape that corresponds to the overall radius of the wheel. The radius of curvature of the rollers is at the center of the larger main wheel.) The effect is that the omni wheel will roll forward, about the main wheel axle, without resistance and will also slide laterally with great ease, by rolling on the smaller rollers that are in contact with a surface. In some embodiments disclosed herein, the holonomic tracking device is connected to an NDI sensor array or other maintenance tool. A respective encoder measures rotation of each omni wheel during holonomic motion. A computer system is programmed with routines that convert relative wheel positions into sensor position and orientation. The tracking methods disclosed herein can be applied to both hand-held and automated NDI scanning. The disclosed holonomic tracking device can also be used in connection with tools other than NDI sensor units, such as marking equipment (painting), drills, bar code scanners, cleaning equipment, lighting, visual and IR cameras and audio speakers.

Standard two-wheel differential odometry is a well-known method for planar position tracking, but it is non-holonomic, meaning that it is subject to motion constraints that restrict movement in one or more directions. This limits free-form motion that would be used for hand-held scanning types of applications.

In contrast, the systems disclosed herein have the ability to track holonomic movement of the device on a surface using omni wheel-based differential odometry. In accordance with one embodiment, a data acquisition device receiver encoder counts from a plurality of encoders, one for each omni wheel. The data acquisition device then processes those encoder counts to derive encoder inputs using simulated encoder pulses suitable for processing by NDI scan software.

In accordance with some embodiments, the data acquisition device is instructed by motion control software to generate quadrature pulses corresponding to changes in X and Y motions of the device. For example, in the case of ultrasonic inspection, these simulated encoder pulses are sent by the data acquisition device to an ultrasonic pulser/receiver. The pulser/receiver sends the simulated encoder pulses to the NDI scan software. The NDI scanning software application converts the simulated encoder pulses into a current X-Y coordinate position, which is used to position the scan imaging data in its proper locations.

Figure 1:
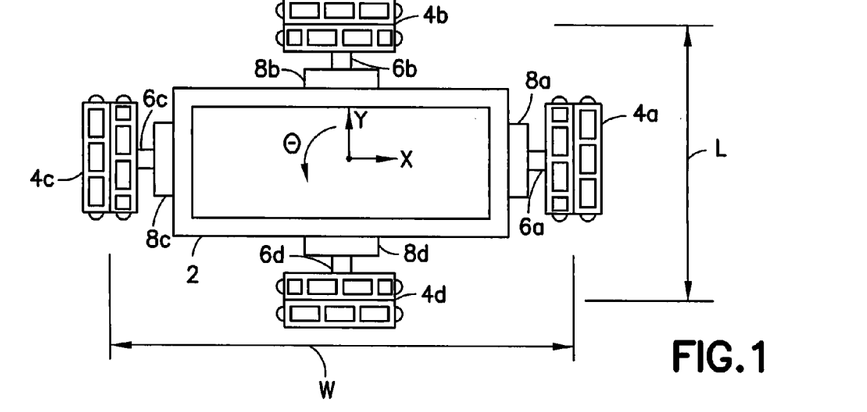
FIG. 1 is a diagram representing a top planar view of some components of an encoder-equipped holonomic-motion device in accordance with one embodiment. This device can be connected to an NDI sensor unit (not shown).

FIG. 1 shows a top planar view of some components of an encoder-equipped holonomic-motion hand-held tracking device in accordance with a four-omni wheel, perpendicular, double-differential configuration. This tracking device can be connected to an NDI sensor unit (not shown). The device shown in FIG. 1 comprises a rectangular frame 4 and four double-row omni wheels 4a-4d rotatably mounted to frame 4 by means of respective axles 6a-6d and axle bearings (not shown). In this particular implementation, axles 6a and 6c are coaxial; axles 6b and 6d are coaxial; and axles 6a, 6c are perpendicular to axle 6b, 6d. Respective encoders 8a-8d measure rotation of the omni wheel 4a-4d. As the omni wheels roll on a surface, the encoders 8a-8d send encoder pulses representing respective encoder counts to an operations control center via an encoder cable (not shown in FIG. 1, but see item 36 in FIG. 6) after each incremental rotation of each omni wheel. These encoder pulses will be received by a computer system (not shown in FIG. 1) that derives the X and Y coordinates of the device. This embodiment shows double-row omni wheels (which may improve rolling smoothness in some conditions), but single-row omni wheels may also be used.

Figure 2A:
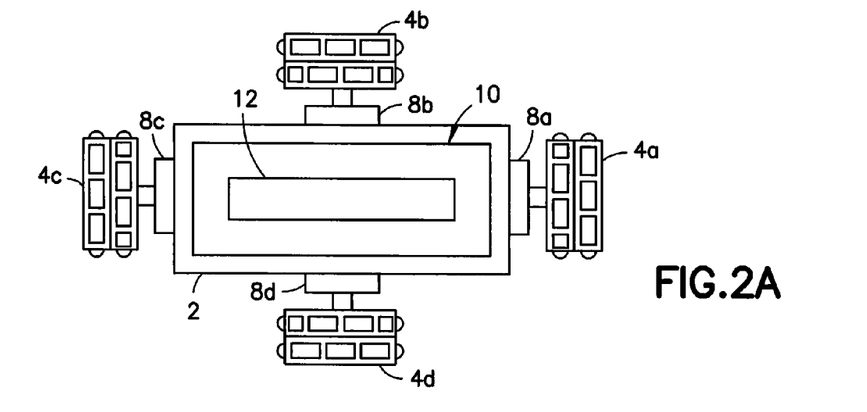
FIGS. 2A and 2B are diagrams respectively representing a top planar view and a front view of a hand-held scanning device comprising an NDI sensor unit connected to an encoder-equipped holonomic-motion device of the type graphically depicted in FIG. 1.
Figure 2B:
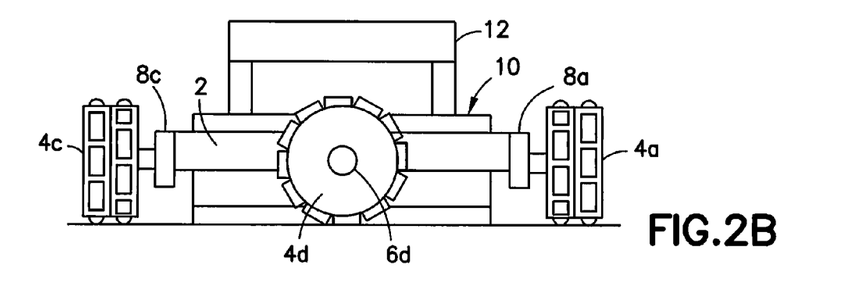

FIGS. 2A and 2B respectively show top planar and front views, respectively, of a hand-held scanning device comprising an NDI sensor unit 10 is rigidly connected to an encoder-equipped holonomic-motion device of the type graphically depicted in FIG. 1. The holonomic motion device is carried by the NDI sensor unit. The NDI sensor unit 10 has a handle 12 attached thereto by means of which the operator can manually move the scanning device in any direction with or without rotation. One or more of the omni wheels/encoder assemblies may be mounted in such a way as to allow compliance between the support frame and wheel-encoder assembly (for example, using linear guides and springs). This allows the wheels to stay in contact with the surface in the event that the surface is not perfectly flat. During manual scanning, encoder 8a will output an encoder count $e_0$ proportional to the angle of rotation of omni wheel 4a; encoder 8b will output an encoder count $e_1$ proportional to the angle of rotation of omni wheel 4b; encoder 8c will output an encoder count $e_2$ proportional to the angle of rotation of omni wheel 4c; and encoder 8d will output an encoder count $e_3$ proportional to the angle of rotation of omni wheel 4d.

The kinematics equations of motion that define the orientation and position of the four-wheel, perpendicular double-differential configuration shown in FIG. 1 will now be described with reference to the dimensions indicated in FIG. 1. The process involves computing the absolute angle, θ, and the changes in relative positions, $\Delta P_x$ and $\Delta P_y$, at each update step, and then using the absolute angle and changes in relative position to compute the absolute position, $P_x$, and $P_y$, of one point on the device (e.g., a common center point) as shown below:

$$\theta = \frac{2\pi R(e_0 - e_1 - e_2 + e_3)}{c(W + L)} \tag{1}$$

where R is the radius of the omni wheel, $e_i$ is each encoder count (i=0 through 3) relative to the starting location, c is the number of encoder counts per rotation, W is the width (i.e., the distance between one set of omni-wheels), and L is the length (the distance between the other set of omni-wheels).

$$\Delta P_x = \pi R(\Delta e_1 + \Delta e_3)/c \tag{2}$$

$$\Delta P_y = \pi R(\Delta e_0 + \Delta e_2)/c \tag{3}$$

where $\Delta e_i = e_i - e_{i\_last}$. Equations (2) and (3) are computed at every update cycle. Then using θ, $\Delta P_x$ and $\Delta P_y$, the absolute position can be computed using the following rotation matrix formulation:

$$\begin{bmatrix} P_x \\ P_y \end{bmatrix} = \begin{bmatrix} P_{x\_last} \\ P_{y\_last} \end{bmatrix} + \begin{bmatrix} \cos\theta & -\sin\theta \\ \sin\theta & \cos\theta \end{bmatrix} \begin{bmatrix} \Delta P_x \\ \Delta P_y \end{bmatrix} \tag{4}$$

Figure 3:
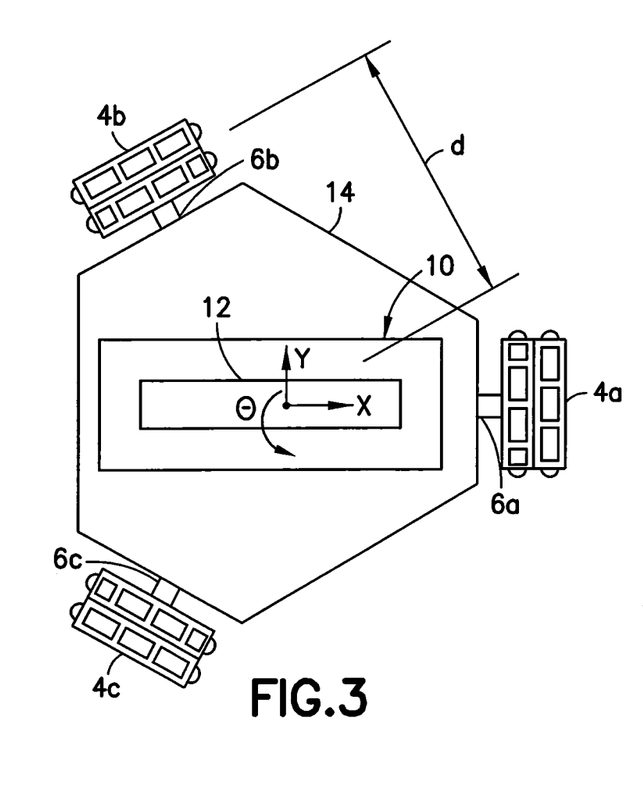
FIGS. 3 and 4 are diagrams representing top planar views of respective hand-held scanning devices having three omni wheels in accordance with alternative embodiments.
Figure 4:
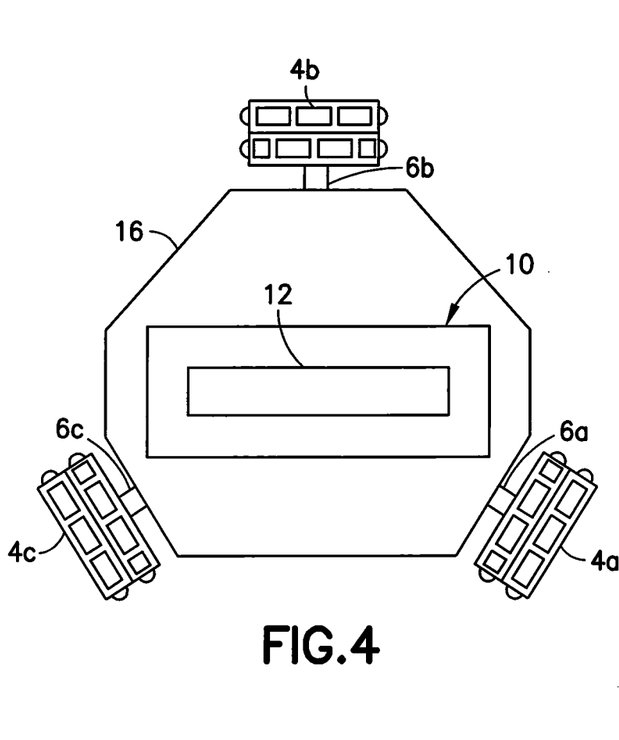

FIGS. 3 and 4 show top planar views of respective hand-held scanning devices having three double-row omni wheels 4a-4c in accordance with alternative embodiments. The device shown in FIG. 3 comprises a six-sided frame 14, while the device shown in FIG. 4 comprises a multi-sided frame 16. In both embodiments, three double-row omni wheels 4a-4c are rotatably mounted to the frame by means of respective axles 6a-6c and axle bearings (not shown). In each implementation, the axes of axles 6a-6c are disposed at 120° with respect to each other. Respective encoders 8a-8c encode incremental rotations of each omni wheel 4a-4c. In both embodiments, the frame is connected to an NDI sensor unit 10 that has a handle 12 that can be gripped by the operator, who then can move the scanning device manually in any direction with or without rotation. As with the four wheel designs, single-row omni wheels could be used instead of the double-row wheels if needed. Although a mechanism for enabling compliance between the omni wheel/encoder sub-assemblies and the frame can be included, this is less necessary in a three-wheel configuration, unless the system is used on highly contoured surfaces.

In a similar way as was done above for a device having a four-omni wheel, perpendicular, double-differential configuration, the kinematics equations can be derived for a platform with three equally spaced omni wheels arranged in a circular-tangent configuration as shown in FIGS. 3 and 4:

$$\theta = \frac{2\pi R(e_0 + e_1 + e_2)}{dc} \tag{5}$$

where the variable d is the distance from each wheel to the common center point (see FIG. 3).

$$\Delta P_x = \pi R(-2\Delta e_0 + \Delta e_1 + \Delta e_2)/c \quad (6)$$

$$\Delta P_y = \sqrt{3}\pi R(-e_1 + \Delta e_2)/c \quad (7)$$

The absolute position for the three-wheel system is computed using Eq. (4).

Figure 5A:
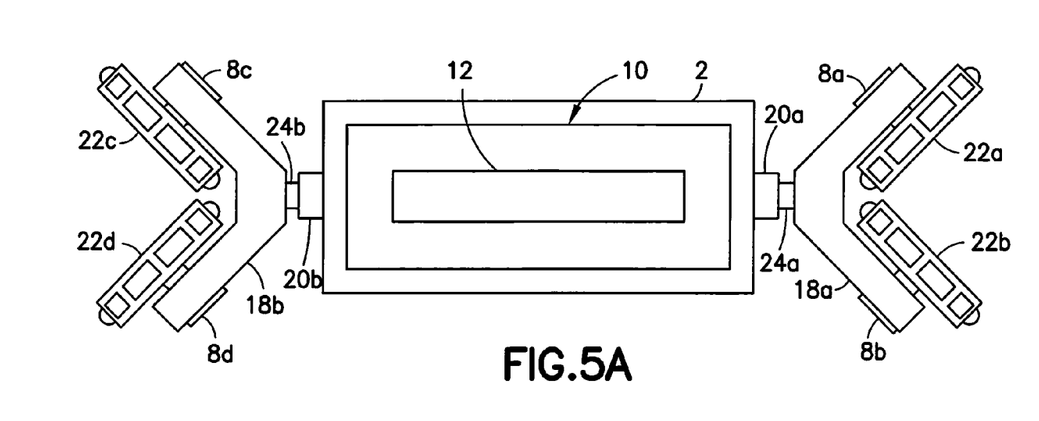
FIGS. 5A and 5B are diagrams respectively representing a top planar view and a front view of a hand-held tracking device comprising an NDI sensor unit connected to an encoder-equipped holonomic-motion device in accordance with another embodiment. In this alternative embodiment, the holonomic-motion device has four omni wheels arranged in a bogie configuration.
Figure 5B:
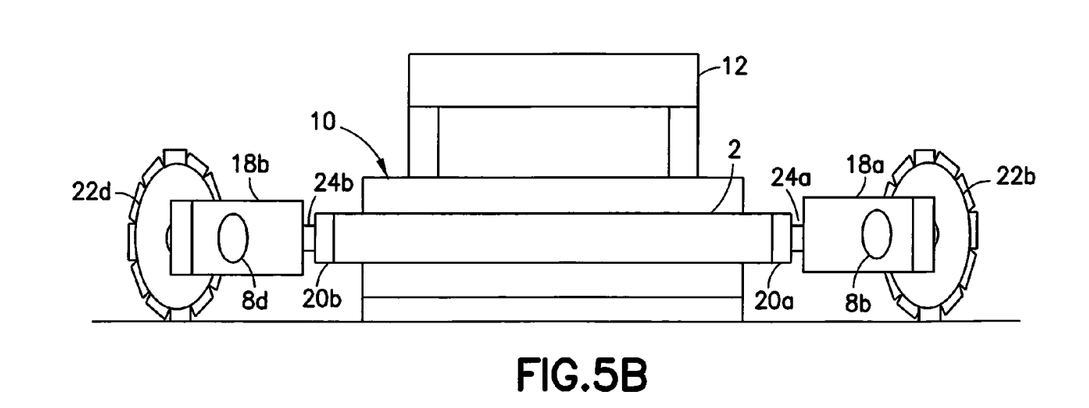

Other wheel configurations are possible, such as the bogie configuration shown in FIGS. 5A and 5B, as well as many other similar configurations. Although the equations for orientation and relative translation will be different, the absolute position computation follows the same process as the two configurations shown above, involving the initial computation of the relative positions and absolute angle, and then using Eq. (4) to compute the absolute position.

In contrast to the embodiments depicted in FIGS. 2A, 3 and 4, which use double-row omni wheels, the embodiment shown in FIGS. 5A and 5B uses single-row omni wheels 22a-22d. The double row wheels have the advantage of smoother rolling over relatively flat surfaces, but the added width can be a disadvantage in some situations, such as in tight spaces or on highly curved surfaces.

The embodiment shown in FIGS. 5A and 5B comprises a rectangular frame 2 having a pair of axle mounting brackets 20a, 20b at opposing ends thereof. These mounting brackets 20a, 20b respectively attach pivot axles 24a, 24b of each bogie to the frame 2 that attaches to the NDI sensor unit 10. Respective carriages 18a, 18b are affixed to the ends of the pivot axles 24a, 24b, which allows the bogies (also known as carriages) 18a, 18b to rotate relative to frame 2. One pair of omni wheels is mounted to one carriage; another pair of omni wheels is mounted to the other carriage. Omni wheel 22a is attached to a shaft of a rotational encoder 8a, which is mounted to one arm of carriage 18a, while omni wheel 22b is attached to a shaft of a rotational encoder 8b, which is mounted to the other arm of carriage 18a. As the omni wheels 22a, 22b ride over a non-planar surface, the carriage 18a is free to rotate as necessary to keep omni wheels 22a, 22b in contact with the non-planar surface. The same is true for rotatable carriage 18b, one arm of which supports rotational encoder 8c and omni wheel 22c, while the other arm supports rotational encoder 8d and omni wheel 22d. Preferably the axes of rotation of omni wheels 22a, 22b are mutually perpendicular, while the axes of rotation of omni wheels 22c, 22d are respectively parallel to the axes of rotation of omni wheels 22a, 22b.

The electrical connections for sending encoder outputs to a data acquisition device and sensor outputs to an NDI processor are not shown in any of FIGS. 1, 2A, 2B, 3, 4, 5A and 5B. In the alternative, encoder data could be sent wirelessly.

Figure 6:
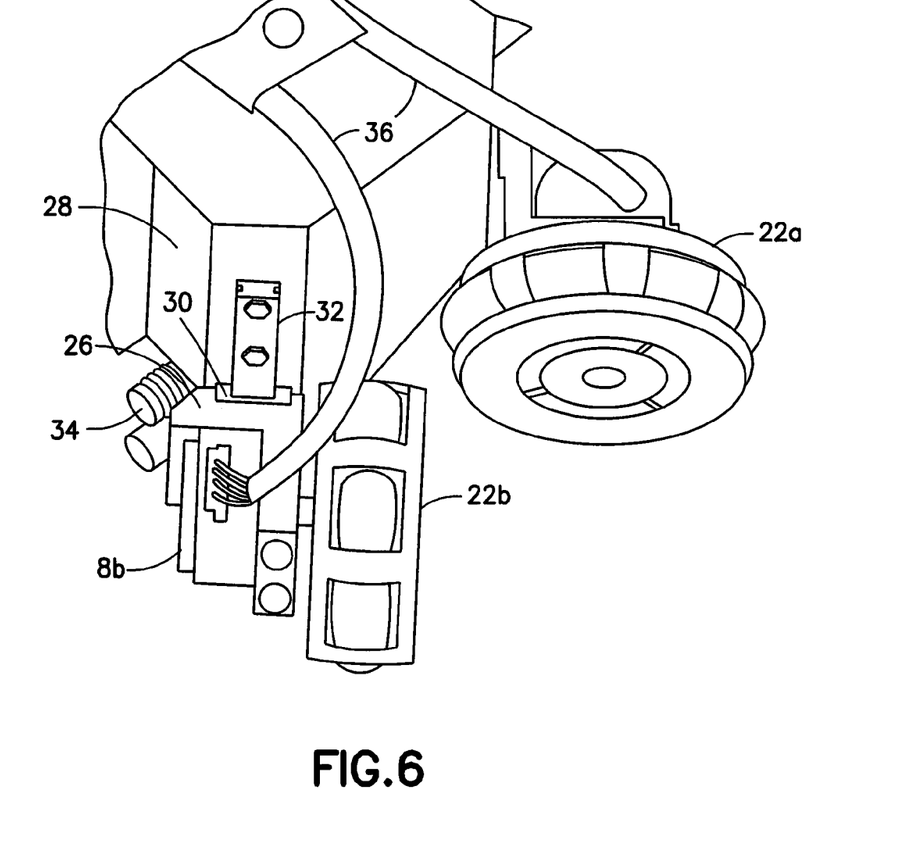
FIG. 6 is a diagram showing an omni wheel mounted to a frame by means of a spring-loaded linear motion guide that allows only vertical displacement of the omni wheel relative to the frame.

In accordance with alternative embodiments, each omni wheel can be pivotably mounted to a mounting bracket that is vertically slidable relative to the frame. FIG. 6 shows an omni wheel 22b pivotably mounted to a mounting bracket 26 that is vertically slidable relative to a frame 28 by means of a spring-loaded recirculating-ball-bearing linear motion guide comprising a slider 30 and a rail 32. In this implementation, the mounting bracket 26 is attached to slider 30, while rail 32 on which slider 30 slides is attached to the frame 28. This allows the encoder/omni wheel subassembly (8b/22b) to displace vertically relative to the frame 28. A spring 34 is attached between the mounting bracket 26 and the frame 28 to urge the omni wheel 22b downward into contact with the upper surface of the object being scanned, which upper surface may be non-planar. The encoder 8b outputs encoder counts to a data acquisition device (not shown in FIG. 6) via electrical cables 36.

Figure 7:
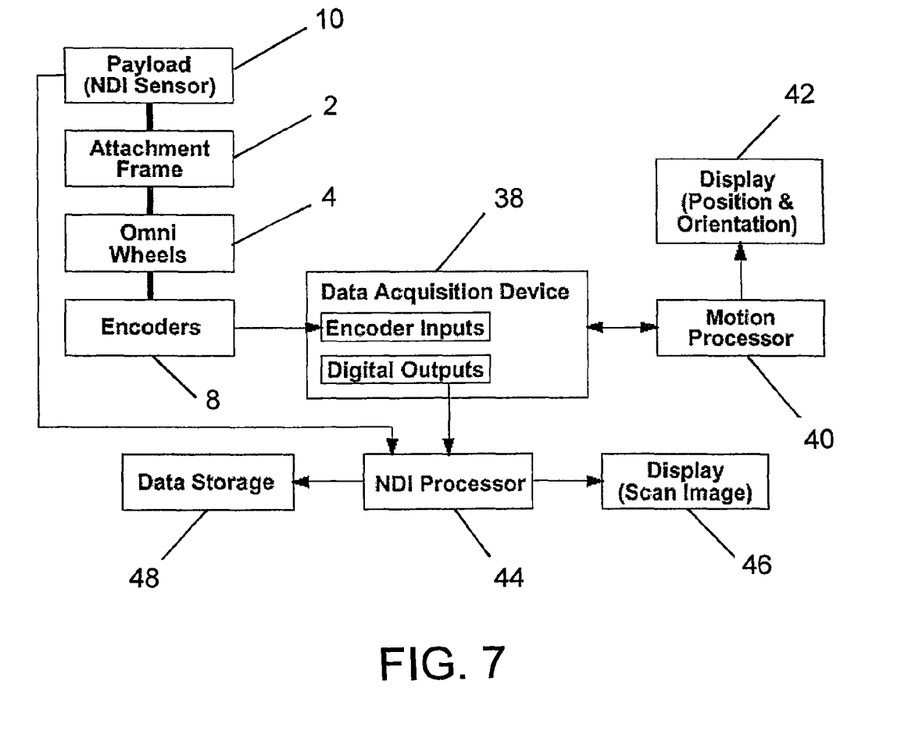
FIG. 7 is a block diagram showing major components of a system for tracking a holonomic-motion NDI sensor unit in real-time in accordance with one embodiment.

FIG. 7 shows major components of a system for real-time tracking of a holonomic-motion device comprising a frame 2 coupled to a plurality of omni wheels 4. In accordance with the embodiment shown in FIG. 7, the frame 2 is connected to an NDI sensor unit 10. As previously described, the rotation of each omni wheel 4 is measured by a respective encoder 8. The encoder data (i.e., counts) is output from encoders 8 to a data acquisition device 38 via electrical signal cables (not shown in FIG. 7). The data acquisition device 38 is electrically connected to a motion processor 40. The motion processor 40 receives the encoder data from the data acquisition device 38 and calculates X and Y absolute position data (which is defined in the coordinate system of the part being scanned) using the kinematics equations set forth above, thereby deriving the absolute position of the NDI sensor unit 10. The motion processor 40 then converts only the X and Y absolute position data into a quadrature pulse form (which comprises two phase-shifted series of high (1) or low (0) values). Optionally the motion processor 40 can show position and orientation information on a display screen 42. In alternative embodiments, the motion processor may be integrated with the data acquisition device.

The data acquisition device 38 converts the quadrature pulse instructions from the motion processor 40 into electrical signals that simulate encoder pulses. The simulated encoder pulses are sent over signal wires to an NDI processor 44. The simulated encoder pulses are received by the NDI processor 44, which decodes the simulated encoder pulses into position data representing the position of the NDI sensor unit 10 relative to the coordinate system of the part being scanned. The NDI processor 44 also receives NDI scan imaging data from the NDI sensor 10. This NDI scan imaging data is aligned into a common coordinate system using the X-Y position data received as simulated encoder pulses. The NDI processor 44 may also display a scan image on a display screen 46 and/or store the resulting aligned NDI scan imaging data in a data storage device 48.

Figure 8:
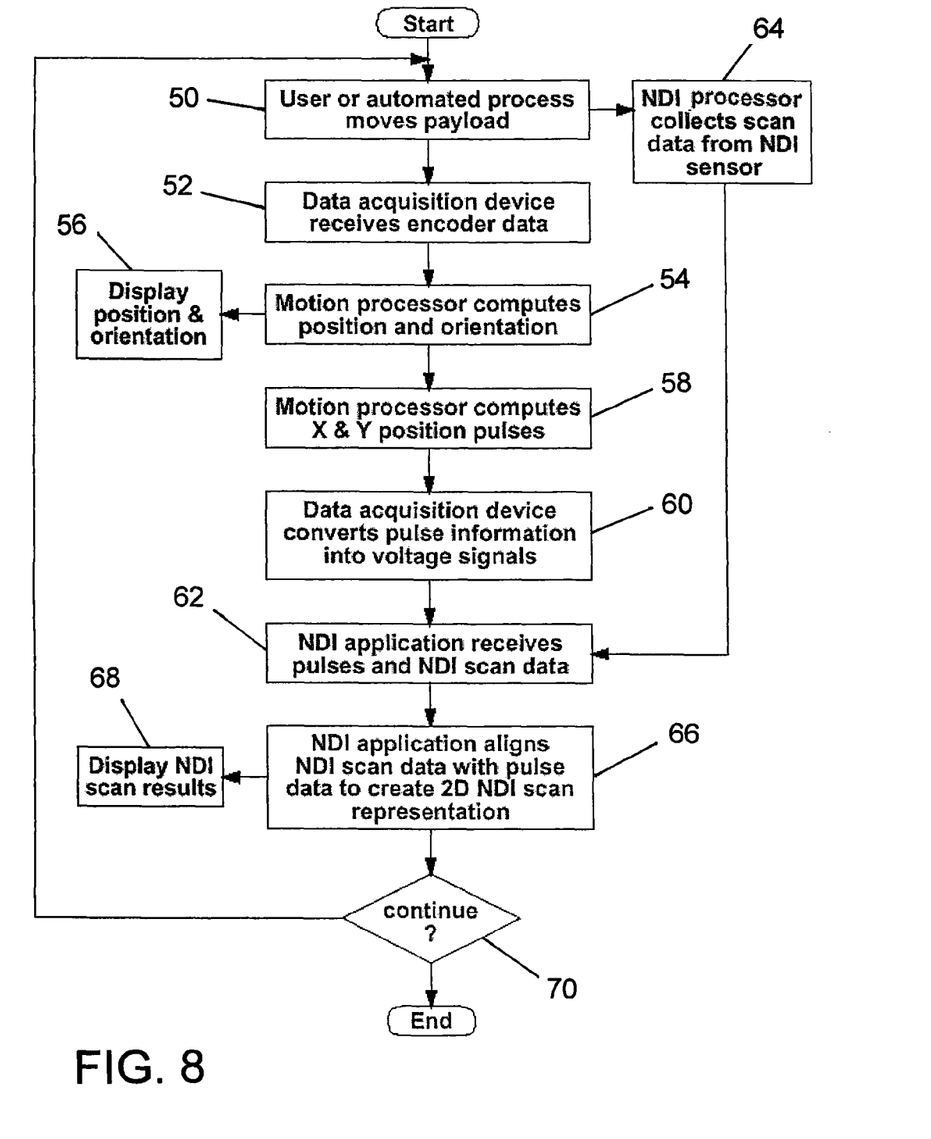
FIG. 8 is a flowchart showing a process for tracking a holonomic-motion NDI sensor unit in real-time in accordance with one embodiment.

FIG. 8 is a flowchart showing steps of a process for tracking a holonomic-motion NDI sensor unit in real-time in accordance with one embodiment. This process is applicable to free-form motion produced by either a hand-held device or an automated device such as a motorized crawler vehicle. The sequence of steps involves a continuous loop. First, the NDI sensor unit is moved by the operator or by an automated process (step 50). As the NDI sensor unit moves, encoder data is received by the data acquisition device (step 52). Then the motion processor uses that encoder data to compute the position and orientation of the NDI sensor unit (54). The position and orientation of the NDI sensor unit may be displayed on a display screen (step 56). Then the motion processor computes the X and Y position encoder pulses corresponding to the absolute position data computed in step 54 (step 58). The data acquisition device then converts that X-Y position data into simulated encoder pulses acceptable to the NDI processor (step 60). In the meantime, the NDI processor collects scan imaging data from the NDI sensor unit while it is being moved (step 64). The NDI processor runs an NDI application that receives the simulated encoder pulses from the data acquisition device and the scan imaging data sensor system (step 62), and aligns the scan imaging data using the X-Y position information carried by the simulated encoder pulses (step 64). An optional display screen may be attached to the sensor platform or other location accessible to the operator to provide position and orientation feedback during operation of the system by displaying the NDI scan image (step 68).

The process generally described with reference to FIG. 8 will now be described in more detail with reference to FIG. 7. In one implementation, the data acquisition device 38 sends the encoder data to the motion processor 40 through API function calls. In accordance with one implementation, the data acquisition device may be a USB4 encoder data acquisition USB device commercially available from US Digital, Vancouver, Wash. In this implementation, the data acquisition device 38 sends the data through a USB interface (over a USB cable), but other data acquisition devices may use other communications interfaces (e.g., a PCI slot inside the computer, a serial communications interface, Express Card, PCMCIA, or an Ethernet interface). The signals that the data acquisition device 38 sends to the application running on the motion processor 40 are converted forms of the encoder data. Typically, this means conversion into data packets that are sent over the communication interface to the motion processor 40 and converted into integers or floating point numbers by the API. The application running on the motion processor 40 makes a request for data from the data acquisition device 38 and gets back integers or floating point numbers (for example, for an encoder, the application would request the current number of counts for a specific encoder and get back an integer representing the number of counts in the memory register in data acquisition device 38 that is associated with that encoder).

The motion processor 40 can also request that the data acquisition device 38 generate electrical signals in the form of voltages. These electrical signals are then sent by the data acquisition device 38 to the NDI processor 44. Because the NDI processor is of a type that expects pulses from an encoder, the application running on motion processor 40 is programmed to compute the number and frequency of the pulses required, and then request that the data acquisition device 38 send out simulated encoder pulses in terms of high and low electrical voltages.

The NDI processor 44 converts the simulated encoder pulses onto a current X, Y position in accordance with the formulas:

$$X\_pos = num\_of\_x\_pulses\_received * x\_scale\_factor$$

$$Y\_pos = num\_of\_y\_pulses\_received * y\_scale\_factor$$

where each scale factor is a small number (e.g., on the order of 0.01 inch per pulse). This X, Y position is updated many times per second.

At the same time the NDI sensor unit 10 is capturing inspection data (e.g., scan imaging data). In the case where ultrasonic detection is being utilized, data from each element of a linear array of ultrasonic elements can be acquired. These elements make up an array that is analogous to a row of pixels on a computer monitor (where each row is offset from the next by defining the starting X, Y position of the first pixel and when all the rows are displayed in proper order, a full image can be displayed). Each time the linear array of ultrasonic elements is moved a predefined distance (how far depends on the resolution requested by the operator), the NDI processor 44 receives a new scan strip of data from the NDI sensor unit 10 (representing a "row" of pixel data) via an electrical cable (shown as a line with an arrow from NDI sensor 10 to NDI processor 44 in FIG. 7). The scan strip data is saved to memory (i.e., data storage device 48). The NDI processor executes a program that uses the current X_pos and Y_pos data derived from the pulse data received from the data acquisition device 38 to locate the starting point in the image where to place the row of pixels. The NDI processor 44 associates the position data and the scan imaging data, and then used that associated data to assemble a two-dimensional image of the object being scanned for display on display screen 46.

Figure 9:
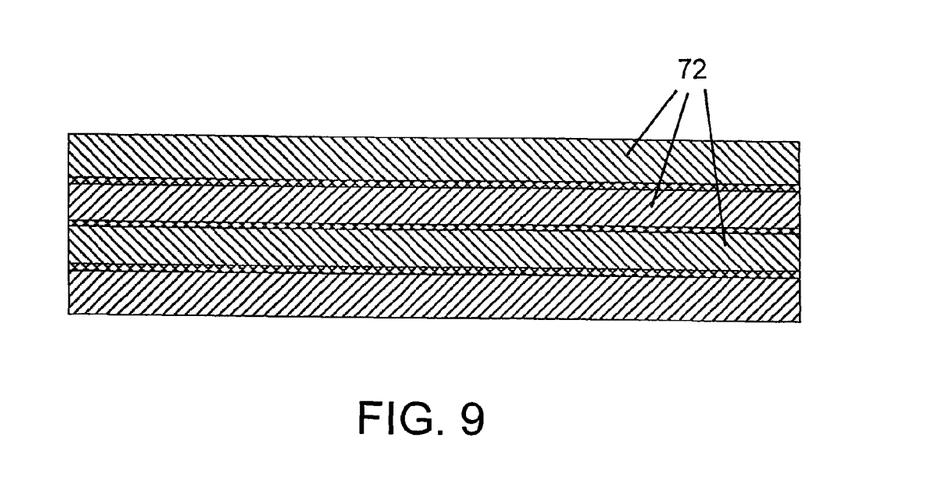
FIG. 9 is a diagram showing merger of strips of scan data from multiple passes slightly offset from each other to produce an accurate, contiguous representation of large inspected areas using a small scanning sensor array.

When X and Y dimensions are tracked, a more accurate representation of the motion that the operator produced during the scan is achieved. As depicted in FIG. 9, this also allows the scanning application to merge strips 72 of scan data from multiple passes slightly offset from each other in order to produce an accurate, contiguous representation of large inspected areas using a small scanning sensor array.

In the case where the NDI sensor unit 10 comprises an array of ultrasonic transducers, the NDI processor 44 provides activation pulses to the ultrasonic transducers, in which case the arrow between blocks 10 and 44 in FIG. 7 would be double-headed to indicate the flow of pulses in one direction and acquired scan imaging data in the other direction. The NDI processor 44 sends electrical pulses to the transducers, which convert them into ultrasonic pulses. The returning ultrasonic pulses are converted at the array back into electrical pulses that are sent back to the NDI processor 44 for measurement.

The above-described simulated encoder pulse method allows the X-Y motion data to be input into any NDI scanning application that accepts encoder inputs, without modification to the NDI scan application. The position update process happens continuously as the user or automated system moves the NDI sensor unit over the scanned object.

Note that in the quad-wheel, double-differential configuration shown in FIG. 1, it is possible to get an approximation of the X and Y motions by using two adjacent encoders without having to use the data acquisition device if the system has physical constraints to prevent change in orientation from occurring. If the vehicle orientation does change, then this method would result in errors that will build up as the orientation changes.

Any dead-reckoning solutions (such as the odometry-based solutions described here) will have measurement inaccuracies due to small errors that build up over time. These can be caused by systematic errors in the device (e.g., one omni wheel is not perfectly aligned) or disruptions caused by unexpected changes in the environment. A loop-closure calibration process can be used with this system to reduce systematic errors. It can also be used at run time to give the operator an estimate of error. For example, the tracking device is placed at a starting location and then moved away and then back to the starting location. If the system computes that the final location is different than the starting location, then this difference can be used to compensate for the error in the tracking data. Additional correction using external reference measurements can be used to improve absolute position tracking.

The NDI sensor unit can be any sensor that collects inspection data from a location or area of a structure. It can be touching or nearly touching the structure (ultrasonic, eddy current, magnetic, microwave, x-ray backscatter, etc.). It can be a single transducer or an array (linear or multiple dimension).

The holonomic tracking device disclosed above can also be used to track the holonomic motion of tools other than NDI sensor units, such as marking equipment (painting), drills, bar code scanners, cleaning equipment, lighting, visual and IR cameras and audio speakers.

The holonomic motion tracking methodology described in detail above has equal application to automated holonomic or non-holonomic motion crawler vehicles. One common type of holonomic vehicle configuration uses a type of wheel called a Mecanum wheel to drive the vehicle. A Mecanum wheel is a type of wheel with multiple individual rollers that, when used in pairs, allows vehicle motion in any direction (i.e., holonomic motion). In one known implementation, the crawler vehicle comprises a frame having four Mecanum wheels, including a front pair of Mecanum wheels and a rear pair of Mecanum wheels, the respective axes of the respective pairs of Mecanum wheels being parallel to each other. In other embodiments, the wheel orientations to the frame may be configured to have camber to address non-planar surfaces (in which case the axles of opposing wheels will not be parallel). In accordance with the teachings herein, a frame of a crawler vehicle may have a set of four omni wheels for tracking vehicle motion and a set of four Mecanum wheels for driving the vehicle under the control of a computer.

A Mecanum-wheeled vehicle can move in any direction while simultaneously rotating. This is possible because of the shape of the wheels. The standard configuration for a Mecanum-wheeled vehicle has four Mecanum wheels (two type "A" and two type "B"). The Mecanum wheels are arranged with the "A" pair on one diagonal and the "B" pair on the other, with the diagonals running through the center of the vehicle. The axes of the rollers on the type "A" Mecanum wheels are at right angles to the axes of the rollers on the type "B" Mecanum wheels.

Such a Mecanum-wheeled vehicle can be made to move in any direction and turn by varying the speed and direction of rotation of each wheel. For example, rotating all four wheels in the same direction at the same rate causes forward or backward movement; rotating the wheels on one side at the same rate but in the opposite direction of the rotation by the wheels on the other side causes the vehicle to rotate; and rotating the Type "A" wheels at the same rate but in the opposite direction of the rotation of the Type "B" wheels causes sideways movement.

While the Mecanum-wheeled vehicle is being driven to move over a surface to be scanned, the rotational encoders coupled to the omni wheels provide encoder data that can used to track the vehicle motion in the manner described above.

The position and orientation of other types of vehicles can also be tracked using the holonomic omni-wheel based system. This includes non-holonomic devices like skid steer vehicles (tanks) and Ackermann steering vehicles (cars). Legged systems like bipeds, quadrupeds, hexapods, etc. can also be tracked by this type of system—at least on surfaces without large obstacles.

The systems disclosed above combine holonomic omni-wheel tracking with NDI. These systems are self-contained (i.e., do not require the setup of additional hardware) and operate in real-time. The systems can be self-calibrated using a loop-closure technique. Rotational encoders coupled to omni wheels provide angular measurement data that can be used to derive the position, orientation, and velocity of a holonomic motion device that can be provided to other analysis systems and to the operator.

The benefits of the methodology described above are manifold. Simultaneous position and orientation tracking gives a more accurate representation of where the scan unit is located, which allows for: (1) input to hardware that receives X and Y data; (2) applications that warn users when they have missed a spot on the scanned surface; and (3) applications that warn users when they are not holding proper orientation. In addition, registration of scan data with a common coordinate system allows: (1) alignment of scan strips; and (2) use with two- or three dimensional visualization displays.

When X and Y dimensions are tracked, a more accurate representation of the motion that the operator produced during the scan is achieved. This also allows the scanning application to merge strips of scan data from multiple passes slightly offset from each other in order to produce an accurate, contiguous representation of large areas using a small scanning array sensor.

While the holonomic motion tracking methodology has been described with reference to various embodiments, it will be understood by those skilled in the art that various changes may be made and equivalents may be substituted for elements thereof without departing from the scope of the teachings herein. In addition, many modifications may be made to adapt the teachings herein to a particular situation without departing from the scope thereof. Therefore it is intended that the claims not be limited to the particular embodiments disclosed herein.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices comprising a processing unit (e.g., a central processing unit) and some form of memory (i.e., computer-readable medium) for storing a program which is readable by the processing unit.

As used in the claims, the term "location" comprises position in a fixed two-dimensional coordinate system and orientation relative to the coordinate system.

The method claims set forth hereinafter should not be construed to require that the steps recited therein be performed in alphabetical order (alphabetical ordering in the claims is used solely for the purpose of referencing previously recited steps) or in the order in which they are recited. Nor should they be construed to exclude any portions of two or more steps being performed concurrently or alternatingly.

The invention claimed is:

1. An inspection system comprising a scanning device, a display device and a computer system, said scanning device and said display device being coupled to communicate with said computer system, wherein said scanning device comprises: a frame; a plurality of omni wheels rotatably coupled to said frame and arranged in a four-omni wheel, perpendicular, double-differential configuration; a plurality of rotational encoders respectively coupled to said plurality of omni wheels for converting rotation of each omni wheel into respective encoder data; and an inspection unit connected to said frame, and wherein said computer system is programmed to execute the following operations:
(a) computing an absolute angle $\theta$ representing an orientation of the scanning device relative to a coordinate system based in part on said encoder data;
(b) computing relative changes in X and Y positions $\Delta P_x$ and $\Delta P_y$ of a point on the scanning device relative to said coordinate system based in part on said encoder data;
(c) computing an absolute position of the point on the scanning device relative to said coordinate system based in part on said computed absolute angle and said computed changes in X and Y positions;

(d) controlling said inspection unit to acquire inspection data;

(e) controlling said display device to display an image in which the inspection data is arranged based on the respective absolute angle and absolute position of the point on said scanning device when each inspection datum was acquired.

2. The inspection system as recited in claim 1, wherein said computer system is further programmed to execute the following operations:

converting the computed absolute angles and absolute positions into simulated encoder pulses; and correlating the inspection data with the simulated encoder pulses, wherein said displaying operation arranges the inspection data in accordance with the results of said correlating operation.

3. The inspection system as recited in claim 2, wherein said simulated encoder pulses are quadrature pulses suitable for processing by inspection scan software.

4. The inspection system as recited in claim 3, wherein said computer system is further programmed to convert the simulated encoder pulses into X-Y coordinate positions, wherein said correlating operation comprises correlating the inspection data with the X-Y coordinate positions.

5. The inspection system as recited in claim 1, wherein the absolute position of the point on the inspection unit is computed using the following rotation matrix formulation:

$$\begin{bmatrix} P_x \\ P_y \end{bmatrix} = \begin{bmatrix} P_{x\_last} \\ P_{y\_last} \end{bmatrix} + \begin{bmatrix} \cos\theta & -\sin\theta \\ \sin\theta & \cos\theta \end{bmatrix} \begin{bmatrix} \Delta P_x \\ \Delta P_y \end{bmatrix}$$

wherein $P_{x\_last}$ and $P_{y\_last}$ represent a last absolute position of the point on the inspection unit.

6. The inspection system as recited in claim 5, wherein the absolute angle $\theta$ is computed using the following relationship:

$$\theta = \frac{2\pi R(e_0 - e_1 - e_2 + e_3)}{c(W + L)} \quad (1)$$

where R is a radius of each omni wheel, $e_i$ is each encoder count (i=0 through 3) relative to a starting location, c is a number of encoder counts per rotation, W is a distance between one pair of said omni wheels, and L is a distance between another pair of said omni wheels.

7. The inspection system as recited in claim 6, wherein the changes in relative positions $\Delta P_x$ and $\Delta P_y$ at each update step are computed using the following functions:

$$\Delta P_x = \pi R(\Delta e_1 + \Delta e_3)/c$$

$$\Delta P_y = \pi R(\Delta e_0 + \Delta e_2)/c$$

where $\Delta e_i = e_i - e_{i\_last}$ and $e_{i\_last}$ is the last encoder count.

8. The inspection system as recited in claim 1, wherein said inspection unit comprises a sensor array.

9. The inspection system as recited in claim 8, wherein said sensor array comprising a multiplicity of ultrasonic transducers.

10. The inspection system as recited in claim 1, wherein said computer system is programmed to repeat operations (a) through (c) at regular intervals of time to provide absolute angles and absolute positions of the device over a period of time.

11. A method for tracking an inspection unit that is coupled to four omni wheels arranged in a perpendicular, double-differential configuration, the method comprising:

(a) moving the inspection unit while the omni wheels are in contact with a surface of a part to be inspected;

(b) converting rotation of each omni wheel into respective encoder data during movement of the inspection unit;

(c) acquiring inspection data using the inspection unit;

(d) computing an absolute angle $\theta$ representing an orientation of the inspection unit relative to a coordinate system of the surface based in part on said encoder data;

(e) computing relative changes in X and Y positions $\Delta P_x$ and $\Delta P_y$ of a point on the inspection unit relative to the coordinate system of the surface based in part on said encoder data;

(f) computing an absolute position of the point on the inspection unit relative to the coordinate system of the surface based in part on said computed absolute angle and said computed changes in X and Y positions; and (g) displaying an image in which the inspection data is arranged based on the respective absolute angle and absolute position of the point on the inspection unit when each inspection datum was acquired.

12. The method as recited in claim 11, further comprising:

converting the computed absolute angles and absolute positions into simulated encoder pulses; and correlating the inspection data with the simulated encoder pulses, wherein said displaying step arranges the inspection data in accordance with the results of said correlating step.

13. The method as recited in claim 12, wherein said simulated encoder pulses are quadrature pulses suitable for processing by inspection scan software.

14. The method as recited in claim 13, further comprising converting the simulated encoder pulses into X-Y coordinate positions, wherein said correlating step comprises correlating the inspection data with the X-Y coordinate positions.

15. The method as recited in claim 11, wherein the absolute position of the point on the inspection unit is computed using the following rotation matrix formulation:

$$\begin{bmatrix} P_x \\ P_y \end{bmatrix} = \begin{bmatrix} P_{x\_last} \\ P_{y\_last} \end{bmatrix} + \begin{bmatrix} \cos\theta & -\sin\theta \\ \sin\theta & \cos\theta \end{bmatrix} \begin{bmatrix} \Delta P_x \\ \Delta P_y \end{bmatrix}$$

wherein $P_{x\_last}$ and $P_{y\_last}$ represent a last absolute position of the point on the inspection unit.

16. The method as recited in claim 15, wherein the absolute angle $\theta$ is computed using the following relationship:

$$\theta = \frac{2\pi R(e_0 - e_1 - e_2 + e_3)}{c(W + L)}$$

where R is a radius of each omni wheel, $e_i$ is each encoder count (i=0 through 3) relative to a starting location, c is a number of encoder counts per rotation, W is a distance between one pair of said omni wheels, and L is a distance between another pair of said omni wheels.

17. The method as recited in claim 16, wherein the changes in relative positions $\Delta P_x$ and $\Delta P_y$ at each update step are computed using the following functions:

$$\Delta P_x = \pi R(\Delta e_1 + \Delta e_3)/c$$

$$\Delta P_y = \pi R(\Delta e_0 + \Delta e_2)/c$$

where $\Delta e_i = e_i - e_{i\_last}$ and $e_{i\_last}$ the last encoder count.

18. The method as recited in claim 11, wherein steps (a), (b), and (d) through (f) are repeated at regular intervals of time to provide absolute angles and absolute positions of the device over a period of time.

19. The method as recited in claim 11, further comprising using said computed absolute angle and absolute position to position and orient a three-dimensional model of the inspection unit in a virtual environment.

20. An apparatus comprising: a frame; a plurality of omni wheels rotatably coupled to said frame and arranged in a four-omni wheel, perpendicular, double-differential configuration; a plurality of rotational encoders respectively coupled to said plurality of omni wheels for generating encoder counts representing angles of rotation of said omni wheels; an inspection unit connected to said frame; and a data acquisition device connected to receive encoder counts from said rotational encoders, wherein said data acquisition device is configured to convert the encoder counts to simulated encoder pulses suitable for use by inspection scan software.

21. The apparatus as recited in claim 20, wherein said inspection unit comprises a sensor array.

22. The apparatus as recited in claim 21, wherein said sensor array comprising a multiplicity of ultrasonic transducers.

* * * * *